United States Patent
Ristolainen

(10) Patent No.: US 7,272,427 B2
(45) Date of Patent: Sep. 18, 2007

(54) CONDUCTOR

(75) Inventor: Kimmo Ristolainen, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 500 days.

(21) Appl. No.: 10/296,103

(22) PCT Filed: Jun. 19, 2001

(86) PCT No.: PCT/FI01/00582

§ 371 (c)(1),
(2), (4) Date: Jul. 15, 2003

(87) PCT Pub. No.: WO01/97688

PCT Pub. Date: Dec. 27, 2001

(65) Prior Publication Data

US 2004/0034296 A1    Feb. 19, 2004

(30) Foreign Application Priority Data

Jun. 21, 2000   (FI) .................................. 20001482

(51) Int. Cl.
*A61N 1/04* (2006.01)
(52) U.S. Cl. ...................... 600/372; 607/116
(58) Field of Classification Search ............... 600/382, 600/393, 395, 372, 373; 607/2, 115, 116, 607/117, 119
See application file for complete search history.

(56) References Cited

U.S. PATENT DOCUMENTS

| 4,970,488 A | 11/1990 | Horiike et al. |
| 5,554,176 A * | 9/1996 | Maddison et al. ............. 607/9 |
| 5,690,680 A * | 11/1997 | Settler et al. .................. 607/2 |
| 5,782,241 A | 7/1998 | Felblinger et al. |
| 6,032,671 A * | 3/2000 | Mollenauer et al. ........ 128/898 |

FOREIGN PATENT DOCUMENTS

| DE | 196 37 472 | 3/1998 |
| DE | 199 22 999 | 11/2000 |
| EP | 0 829 883 | 3/1998 |

OTHER PUBLICATIONS

EPO Office Action dated Jun. 18, 2004.
Amendment to EPO dated Sep. 7, 2004.
EPO Office Action dated Sep. 17, 2004.
Amendment to EPO dated Mar. 7, 2005.

* cited by examiner

*Primary Examiner*—Scott M. Getzow
(74) *Attorney, Agent, or Firm*—Andrus, Sceales, Starke & Sawall, LLP

(57) ABSTRACT

A conductor, especially a conductor for measuring bioelectric signals occurring in an MRI environment, which comprises an electrically conductive part made of a non-metal material and a sheath part arranged over it. To produce a light and flexible conductor, the impedance of the conductive part is in the range of 5 to 300 kilo-ohm. The sheath part is arranged to endure a required voltage and the conductor comprises a support part which is made of a substantially inelastic material.

12 Claims, 1 Drawing Sheet

CONDUCTOR

CROSS REFERENCE TO RELATED APPLICATION

The present application is the U.S. national stage application of International Application PCT/FI01/00582, filed Jun. 19, 2001, which international application was published on Dec. 27, 2001 as International Publication WO 01/97688. The International Application claims priority of Finnish Patent Application 20001482, filed Jun. 21, 2000.

SUMMARY OF THE INVENTION

The invention relates to a conductor, especially a conductor intended for measuring bio-electric signals occurring in an MRI environment, which comprises an electrically conductive part made of a non-metal material and a sheath part arranged over it.

EKG measurement refers to measuring the electrical operation of the heart of a living being, such as human being. The measurement is for obtaining information on functional disorders occurring in the heart in different situations. This information obtained through EKG measurement includes the heart rate. At the moment, EKG measurement is a routine procedure in operating theatres and intensive care units in different parts of the world. In EKG measurement, electrodes are placed on the patient's skin, and an EKG monitor measures the voltage difference caused by the operation of the heart and induced between the electrodes. The electric signal generated by the heart is very weak, typically 0.5 mV to 2 mV. This is why EKG measuring instruments are very sensitive and the elimination of external electric interference is very important. Several electrodes are typically connected to the patient, and the configurations formed by them are called connections. Each connection represents a sub-section of the electric operation of the heart. Combining the signals obtained from the connections produces a curve which shows the electric operation of the heart. To obtain an EKG signal, the patient should have at least two electrodes. Generally used EKG connections have 3, 5, 7 or 10 electrodes. The electrodes are typically placed on the patients chest. The EKG signal is transmitted to the monitor over conductors, which are called EKG conductors. The conductors are typically made of a highly conductive material, such as copper.

The significance of EKG measurement increases in different areas of treatment in hospitals, since today different examinations are performed even to patients whose condition is quite poor. One area, in which EKG measurement is needed is magnetic resonance imaging. In MRI, a strong static magnetic field and strong radio-frequency pulses are directed to the patient. An image of a required area can be reconstructed on the basis of the signals received from the patient. Today, MRI is also performed on patients in a very poor condition, who are sedated or under anaesthesia. These patients naturally also need monitoring.

During MRI, conventional EKG conductors can not be used. The strong radio-frequency pulses, RF pulses, used in MRI may induce in galvanic EKG conductors so strong interference currents that they cause serious burns to the patient. The above-mentioned problem can be solved by keeping the conductors and electrodes as far away from the imaging area as possible, or by using non-metal EKG conductors. There are EKG measuring instruments intended for the magnetic resonance imaging environment, i.e. MRI environment, the conductors of which do not contain metal but some other conductive material. The most typical solutions are conductors made of carbon fibre, in which the conductive part is made of a carbon fibre bundle. In such a solution, the impedance level of the conductor is approximately 200 to 500 ohm, which is not, however, enough, since the RF pulses of MRI devices are so strong that in certain conditions so strong currents may be induced even in this type of conductors that burns are caused to the patient. Another alternative is to use conductors made of a flexible circuit board, to which a higher impedance level can be obtained by connecting several connections in series to one conductor. However, this type of solution is poor in usability and ergonomics, because the circuit boards are stiffer than conductors and their edges are sharp. Conductors containing ferromagnetic metals can not be used in an MRI environment, because the magnet may attract them, and when in the imaging field, they cause interference to the magnetic images.

BRIEF DESCRIPTION OF THE INVENTION

It is an object of the invention to provide a conductor, by means of which it is possible to eliminate the drawbacks in prior art. This is achieved by a conductor of the invention. The conductor of the invention is characterized in that the impedance of the conductive part is in the range of 5 to 300 kilo-ohm, that the sheath part is arranged to endure a required voltage, and that the conductor comprises a support part which is made of a substantially inelastic material.

Above all, the invention provides the advantage that the high impedance effectively prevents the currents caused by RF pulses from being induced in the conductor, whereby the patients risk of getting burns is substantially less in comparison with the prior art. In spite of the above-mentioned matter, the invention provides the further advantage that the conductor is very well suited for EKG measurement, for instance, because the EKG signal passes well through the conductor and EKG monitors can process it, because the input impedance of their preamplifiers is considerably higher than in the conductor, typically in the range of giga-ohms. A yet further advantage of the invention is that the conductor of the invention is very flexible and thus well suited for measurement.

BRIEF DESCRIPTION OF THE DRAWING

In the following, the invention will be described in greater detail by means of a preferred embodiment shown in the attached drawing in which.

DETAILED DESCRIPTION OF THE INVENTION

Figure 1:
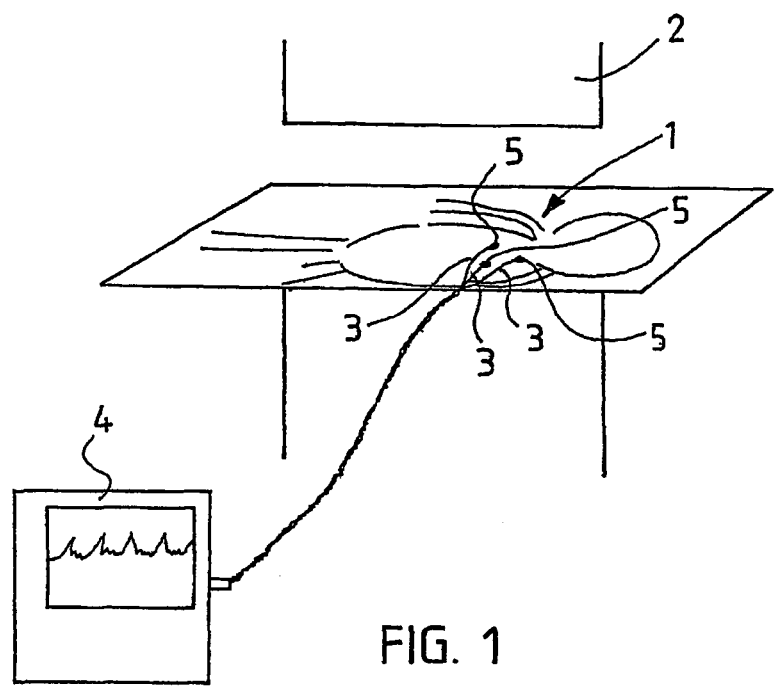
FIG. 1 shows a schematic of measuring an EKG curve during magnetic resonance imaging.

FIG. 1 shows in general a situation in which an EKG curve is measured of a patient 1 during magnetic resonance imaging. Reference numeral 2 in Figure 1 marks the MRI device, reference numerals 3 mark EKG conductors and reference numeral 4 marks a monitor for examining the EKG curve. The EKG conductors are attached to the patient by means of electrode connectors 5 arranged at the ends of the conductors. An EKG conductor set of three conductors forming an entity is formed by the EKG conductors 3, of which there are three in the example of the figure.

Figure 2:
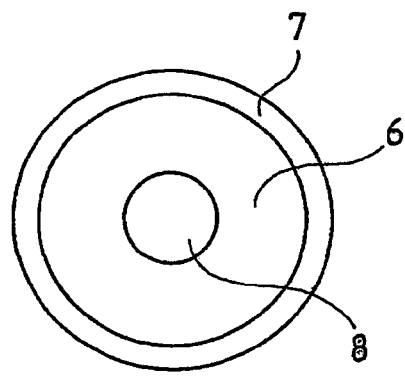
FIG. 2 shows a cross-sectional view of a conductor of the invention.

FIG. 2 shows a conductor of the invention. The invention relates especially to a conductor intended for measuring bio-electric signals occurring in an MRI environment, which has an electrically conductive part 6 made of a non-metal material and a sheath part 7 arranged over it. The impedance of the conductive part 6 is in the range of 5 to 300 kilo-ohm. The sheath part 6 is arranged to endure a required voltage, for instance 5 kV, in compliance with the standard ANSI/AAMI EC53-1995 Section 4.5.1. It has been detected that the sheath part should endure at least a 3-kV voltage, preferably a 5-kV voltage, and most preferably at least a 7-kV voltage. The conductor also comprises a support part 8 which is made of a substantially inelastic material. A substantially inelastic material refers herein to a material which in a load of 50 Newton is allowed to stretch 30%/m. A material which stretches 5%/m is preferable, and the best material is one which stretches 1%/m.

The high impedance effectively prevents the currents caused by RF pulses from inducing in the conductors and thus substantially reduces the risk for burns in comparison with the prior art. So that the RF pulses would not induce currents in the conductors, but it would still be possible to measure the EKG signal, the impedance of the conductors should be in the range of 5 to 300 kilo-ohm. A preferable impedance level is 20 to 100 kilo-ohm and the best impedance level is 40 to 80 kilo-ohm.

Figure 3:
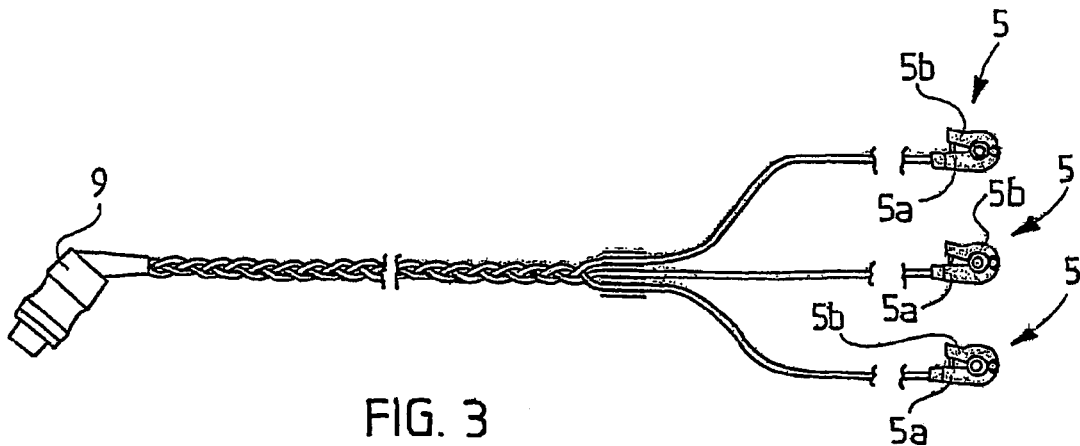
FIG. 3 shows an EKG conductor set formed of conductors of the invention.

A conductor set having three conductors, for instance, can be formed of conductors of the invention, and the conductor set can be used for measuring a 3-connection EKG during magnetic resonance imaging. A schematic of the above-mentioned conductor set is shown in FIG. 3. The conductive part 6 of the conductors in the conductor set is made of a conductive non-metal material having a high impedance, approximately 60 kilo-ohm/conductor, for instance. The conductive non-metal material can be any suitable material, for instance a silicone compound to which carbon particles have been added evenly to produce conductivity. The impedance level of the conductor is determined by the length and diameter of the conductor. The impedance level can be optimized by adjusting the diameter and length of the conductor. If the length of each conductor in the conductor set is selected to be 6.5 m, the diameter of the conductive part of the conductor becomes approximately 2 mm. This diameter includes the support part 8 which is arranged in the middle of the conductor and which can be any substantially inelastic material as described above, for instance a bundle made up of Kevlar fibers. Kevlar is a trademark of E.I. DuPont DeNemours & Company of Wilmington, DE for para-aramid fibers. Kevlar fibers make the conductor substantially inelastic. The support part can also be located elsewhere than on the center axis of the conductor, for instance on the edge of the conductor. With the above-mentioned dimensions, the impedance of the conductor becomes approximately 60 kilo-ohm. If the length of the conductor is increased, its impedance increases correspondingly. If the diameter of the conductive part 6 of the conductor is made smaller, the impedance of the conductor increases correspondingly.

Conductors made of conductive silicone have been tested and compared with prior-art carbon fibre conductors in an MRI environment. In the comparison, both conductors were connected to the imaging object and during the imaging, the voltage induced between two conductors was measured. The voltage of the carbon fibre conductor was 93 V p-p, whereas the voltage of the conductor made of conductive silicone was 2 V p-p. From this, it can be directly deduced that substantially fewer currents were induced in the conductors made of the higher-impedance conductive silicone.

A sheath part 7, which can be any suitable bio-compatible, i.e. non-toxic or non-allergenic, material, is pressed over the conductive material of the conductor of the invention. The material should also have certain voltage endurance properties as described above. Polyurethane is an example of a suitable material. A solution combining conductive silicone and a polyurethane sheath makes the conductor light, flexible and as usable as prior-art galvanic EKG conductors. The conductor of the invention is also suited for use in CT examinations, because the material used in it does not show in an X-ray examination. A CT (computerized tomography) examination is an imaging method where a patient is photographed by means of X-rays and the received signals are used to construct an axial image of the required object.

The embodiment shown in FIG. 3 also shows clearly the electrode connectors 5 arranged at the ends of the conductor, by means of which the conductors are attached to the patient. The connectors are made up of jaw parts 5a made of a non-metal conductive hard material and correspondingly of a second jaw part 5b, which can be made of a suitably colored plastic material, whereby a mechanical contact is made possible and the identification of the electrodes is easy. The jaw part 5a can, for instance, be made of a suitable plastic material to which carbon is added. One end of the conductor set is naturally equipped with an appropriate connector 9, by means of which the conductor set can be connected to a monitor 4, for instance, shown in FIG. 1.

The embodiment described above is in no way intended to limit the invention, but the invention can be modified freely within the scope of the claims. Therefore, it is clear that the conductor of the invention, its details, or the solutions formed by means of the conductor need not necessarily be exactly as described in the figures, and other solutions are also possible. For instance, a layer preventing the generation of static electricity can be formed over the conductor.

The invention claimed is:

1. A conductor for conducting a weak bio-electric signal from a first end of the conductor to a second end of the conductor, the weak bio-electric signal being obtained from a patient electrode connectable to said first end of the conductor, said conductor minimizing attenuation of the conducted, weak bio-electric signal while avoiding the inductive generation of currents in the conductor presenting a risk of injury to the patient when the conductor is used in an environment in which current-inducing electro-magnetic energy is present, said conductor comprising:

an electrically conductive member (6) extending between said first and second ends of the conductor, said electrically conductive member being formed of a solid, non-metallic, conductive material and exhibiting an impedance between said first and second ends in a range of 5 to 300 kilo-ohms;

an insulating sheath member (7) surrounding the exterior of said electrically conductive member, said sheath member having insulating properties that are maintained when the sheath member is subjected to a voltage up to a predetermined magnitude; and a support member (8) extending between said first and second ends of said conductor and comprising a longitudinally substantially inelastic, flexible material.

2. A conductor as claimed in claim 1, characterized in that the impedance of said electrically conductive member (6) is in the range of 20 to 100 kilo-ohm.

3. A conductor as claimed in claim 2, characterized in that the impedance of said electrically conductive member (6) is in the range of 40 to 80 kilo-ohm.

4. A conductor as claimed in claim 1, characterized in that said electrically conductive member (6) is formed of a conductive silicone compound.

5. A conductor as claimed in claim 4, characterized in that carbon particles are uniformly dispersed in the silicone compound.

6. A conductor as claimed in claim 1, characterized in that said insulating sheath member (7) is made of polyurethane.

7. A conductor as claimed in claim 1, characterized in that said support member (8) is arranged along a center axis of the conductor.

8. A conductor as claimed in claim 7, characterized in that said support member (8) is made of Kevlar fibers.

9. A conductor as claimed in claim 1, characterized in that said support member (8) is made of Kevlar fibers.

10. A conductor as claimed in claim 1, characterized in that said first end of the conductor is equipped with an electrode connector (5) which is at least partly made of a conductive hard non-metal material.

11. A conductor as claimed in claim 10, characterized in that the conductive non-metal material of said electrode connector is a plastic material with carbon added to the plastic material.

12. A conductor device for conducting an EKG signal obtained from a patient electrode, said conductor device minimizing attenuation of the conducted, EKG signal while avoiding the inductive generation of currents in the conductor device presenting a risk of injury to the patient when used in an MRI environment, said conductor device comprising:
- an electrode connector (5) suitable for connection to the patient electrode, said electrode connector being formed, at least in part from a plastic material with carbon added to the plastic material;
- an electrically conductive member (6) having first and second ends, said electrode connector being connected to an end of said electrically conductive member, said electrically conductive member being formed of a silicone compound having carbon particles uniformly dispersed therein and exhibiting an impedance between said first and second ends in a range of 40 to 80 kilo-ohms;
- an insulating sheath member (7) surrounding the exterior of said electrically conductive member, said sheath member being formed of polyurethane having insulating properties that are maintained when said sheath member is subjected to a voltage up to at least 3 kV; and
- a support member (8) extending between said first and second ends of said electrically conductive member, said support member being positioned along a center axis of the conductor device and comprising Kevlar fibers.

* * * * *